United States Patent [19]

Abe et al.

[11] Patent Number: 5,177,512
[45] Date of Patent: Jan. 5, 1993

[54] EYEBALL MICROSCOPE

[75] Inventors: Kuniomi Abe; Susumu Fujita, both of Kobe, Japan

[73] Assignee: Konan Camera Research Institute Inc., Hyogo, Japan

[21] Appl. No.: 769,792

[22] Filed: Oct. 2, 1991

[30] Foreign Application Priority Data

Oct. 25, 1990 [JP] Japan .................. 2-289954
Nov. 26, 1990 [JP] Japan .................. 2-324509

[51] Int. Cl.⁵ .............................................. A61B 3/10
[52] U.S. Cl. ................................... 351/221; 351/206; 351/205; 359/368
[58] Field of Search .............. 351/221, 226, 233, 234, 351/214, 216, 205; 359/235, 385, 368, 900, 227, 232, 233, 234, 236

[56] References Cited

U.S. PATENT DOCUMENTS 3,508,813  3/1967  Smith et al. ............. 359/236
4,575,242  3/1986  Akiyama et al. .......... 359/235
5,099,363  3/1992  Lichtman ................. 359/385

FOREIGN PATENT DOCUMENTS 63-50010  10/1988  Japan .

Primary Examiner—Bruce Y. Arnold
Assistant Examiner—Hung Xuan Dang
Attorney, Agent, or Firm—Wegner, Cantor, Mueller & Player

[57] ABSTRACT

An eyeball microscope used for observing or photographing epithelial and endothelial cells and likes of a cornea, which is provided with an illuminating optical system for projecting an illuminating light beam onto an object, an observing optical system for observing or photographing an imaging light beam from the object and parallel slits moving across the optical paths of both optical systems, and arranged to scan the object with optical images of some of the slits and observe imaging beams from the object through other slits, thereby shutting off all unwanted reflecting beams. In this invention, it is suited for both eye observation and photography by composing the slits of plural groups which are mutually different in design.

6 Claims, 5 Drawing Sheets

EYEBALL MICROSCOPE

BACKGROUND OF THE INVENTION

This invention relates to an eyeball microscope and, especially, to such microscope which enables clear observation of epithelial, intermedial and endothelial layers and likes of a cornea in a large field of view.

As shown in FIG. 1, in case of observing an endothelial cell layer 3 of a cornea 2, it had been a general practice in the prior art to illuminate the layer 3 with an illuminating light beam L which was projected through one half of an objective lens of a microscope and observe its imaging beam I through the other half of the objective lens. In this case, however, it was only a small portion W of a microscope field of view D that good observation was obtainable therein, since the imaging beam I of the endothelial cell layer 3 was very low in contrast and, moreover, obstructed by a strong reflecting beam R produced at a corneal surface 4.

In order to remove this disadvantage, an improvement has been proposed by such an invention as disclosed by Japanese patent publication No. S63-50010. According to this invention, as shown in FIG. 2, a narrow domain d of the endothelial cell layer 3 of the cornea 2 is illuminated by an illuminating beam 52 which has passed a certain slit 51a of a light shielding rotary member 51 having slits 51a, 51b, . . . formed therein, and an imaging beam 55 of the domain d is observed through another slit 51b of the rotary member 51. When the rotary member 51 is moved downwards in an arrow direction as shown, the observed domain d moves downwards in the microscope field of view D. Once such observation of the whole filed of view D is completed, the uppermost portion of the field of view D is illuminated through the slit 51b, its imaging beam is observed through a succeeding slit 51c (not shown) and the observed domain moves similarly downwards. Accordingly, if the rotary member 15 is rotated at high speed in the arrow direction, the whole field of view can be observed as shutting off a reflecting beam 56 from the surface 4 of the cornea 2.

However, the invention of FIG. 2 has such a disadvantage in that the observed image is significantly dark as compared with the observable domain W according to the prior art system of FIG. 1, since the field of view is scanned from one end to the other end by a narrow observed domain d as in the case of television image scanned vertically from the top to the bottom by a horizontal scanning line. Reflection of the illuminating beam in the cornea occurs not only at its inner and outer surfaces but also at its intermediate layers. Therefore, it is necessary to remove obstruction of the reflecting beam as much as possible in the case of taking a photograph, though the brighter the image, the easier to see it, in the case of eye observation, even if some reflecting beams are mixed therein. With increase of the width of the slits in the light shielding rotary member, the reflecting beam can be removed more effectively. However, it is undesirable for eye observation and focusing operation since the brightness of the image is reduced. In other words, as to the width of the slits, the wider, the better for eye observation, while the narrower, the better for photography.

Accordingly, an object of this invention is to remove the above-mentioned discrepancy and provide an improved eyeball microscope which can give a preferable condition for both eye observation and photography.

SUMMARY OF THE INVENTION

According to this invention, there is provided an eyeball microscope comprising a first lens to be positioned close to an object or eyeball, second and third lenses located in the rear of respective halves of the first lens, one or two light shielding rotary member or members having substantially parallel slits arranged to traverse the optical axis of the second lens in a conjugate focal plane of the object attributable to the first and second lenses and to traverse the optical axis of the third lens of the object attributable to the first and third lenses, an illuminating optical system including a flashing discharge tube for projecting an illuminating light beam onto the object through at least one of the slits in the light shielding rotary member to form an image of the slits on the object, an observing optical system for observing or photographing an imaging light beam from the object through at least one of the other slits in the light shielding rotary member, and a driving device for rotating the light shielding rotary member or members to move the slit image on the object normally thereto.

As a feature of this invention, the slits in the light shielding rotary member are composed of at least two groups which are mutually different in a slit width and arranged so that the flashing discharge tube is energized to project a strong illuminating light beam when a specific group of the slits of narrower width traverses the optical axes of the second and third lenses, at the time of photographing.

These and other features of this invention will be described in more detail below in conjunction with some embodiments thereof with reference to the accompanying drawings.

BRIEF DESCRIPTION OF THE DRAWINGS

In the drawings.

Throughout the drawings, the same reference numerals are given to corresponding structural components.

DESCRIPTION OF THE PREFERRED EMBODIMENT

Figure 1:
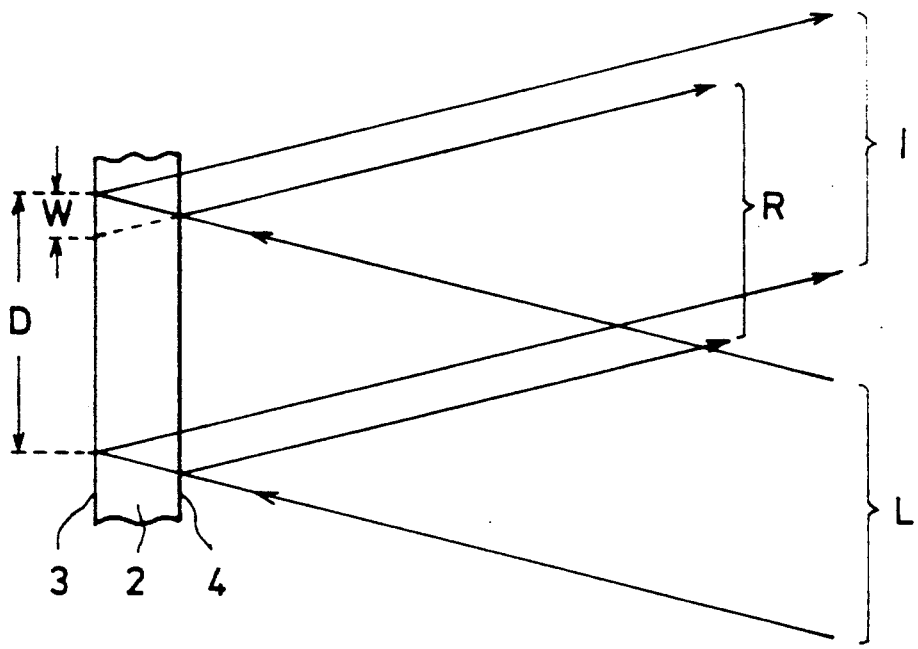
FIGS. 1 and 2 are explanatory diagrams showing mutual relationships of the illuminating, imaging and reflecting light beams in the prior art eyeball microscopes.
Figure 2:
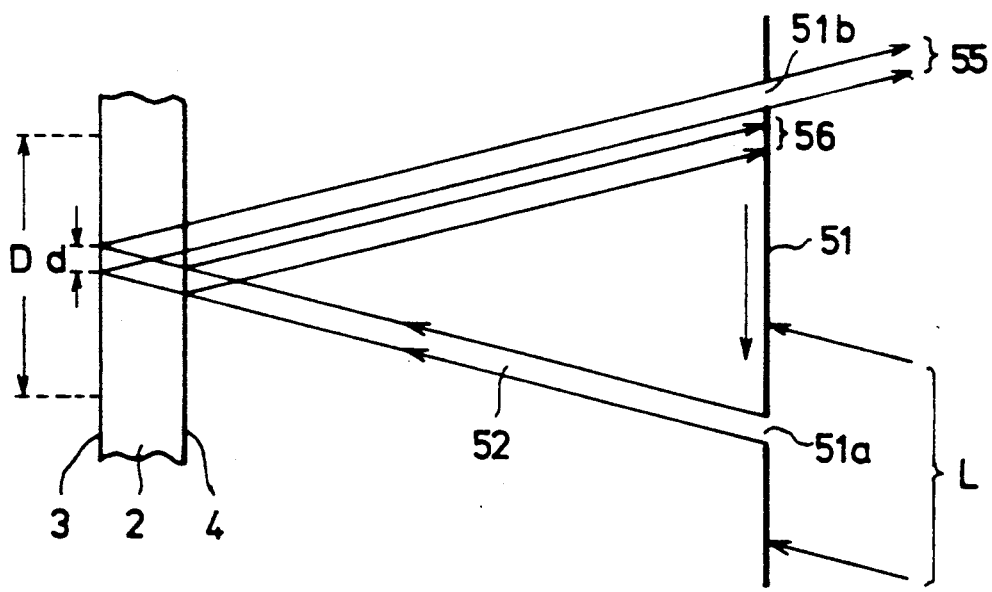
Figure 3:
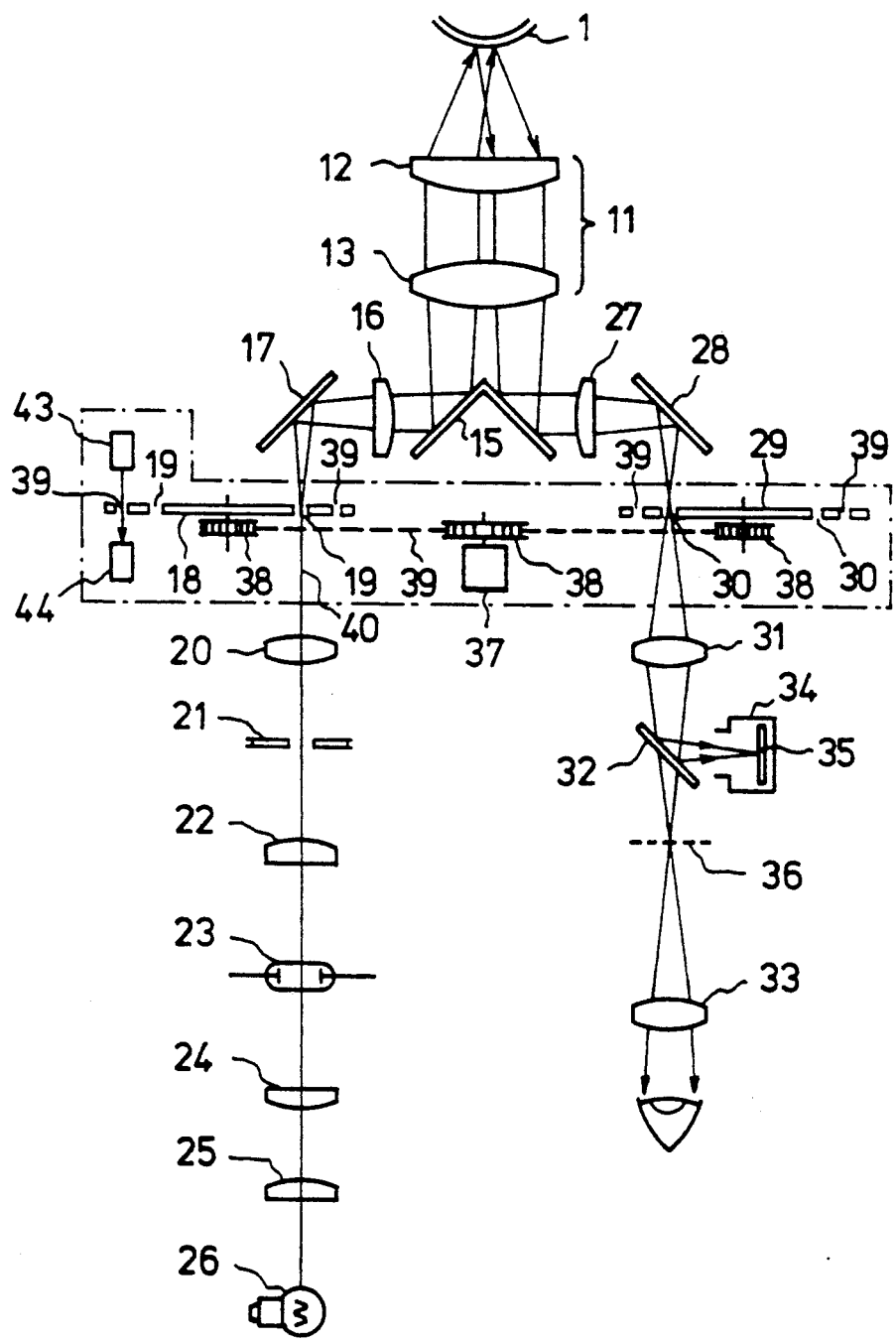
FIG. 3 is a schematic diagram showing a general configuration of an embodiment of the eyeball microscope according to this invention.

Referring to FIG. 3, a common objective lens 11 is composed of a fore lens 12 and a rear lens 13 and a parallel beam region is formed between the fore and rear lenses 12 and 13 for the purpose of preventing a focus of the microscope from changing with movement of the fore lens together with an eyeball 1. An angle mirror 15 is disposed behind the objective lens 11 for dividing an optical path into left and right halves as shown.

The left optical path from the mirror 15 passes a lens 16 and is folded normally again by a mirror 17 in a direction parallel to the optical axis of the objective lens 11 and, thereafter, it passes a slit 19 of a light shielding disc 18, a lens 20, an iris 21 and lens 22, a flash discharge tube 23 and condenser lenses 24 and 25 and reaches a lamp 26. An illuminating beam generated from the lamp 26 is focused by the condenser lenses 25 and 24 at the position of flash discharge tube 23 and again focused by the lens 22 at the position of iris 21 and it is further focused by the lenses 20 and 16 in the vicinity of an entrance pupil of the objective lens 11. The iris 21 has a semicircular opening for preventing random reflection of the illuminating beam colliding against a body tube of the objective lense 11. An image of the slit 19 is projected on the eyeball 1 by the lenses 16 and 11, so that the eyeball 1 is illuminated in a shape of the slit 19.

The right optical path from the mirror 15 passes a lens 27 and is folded again by a mirror 28 in a direction parallel to the optical axis of the objective lens 11 and, thereafter, it passes a slit 30 of another light shielding disc 29, a lens 31 and a half mirror 32 and is observed through an eyepiece 33 and, at the same time, reflected by the half mirror 32 to reach a film 35 in a camera 34. A movable mirror may be used instead of the half mirror 32 to select the optical path for either the eyepiece 33 or the camera 34. Accordingly, an image of the eyeball 1 is formed at a position of the disc 29 by the lens 11, mirror 15, lens 27 and mirror 28 and this image is imaged again on a spatial plane 36 by the lens 31 through the slit 30 and then magnified by the eyepiece 33 for observation. The image on the disc 29 is also imaged again on the film 35 of the camera 34 by the lens 31 and half mirror 32.

Figure 4:
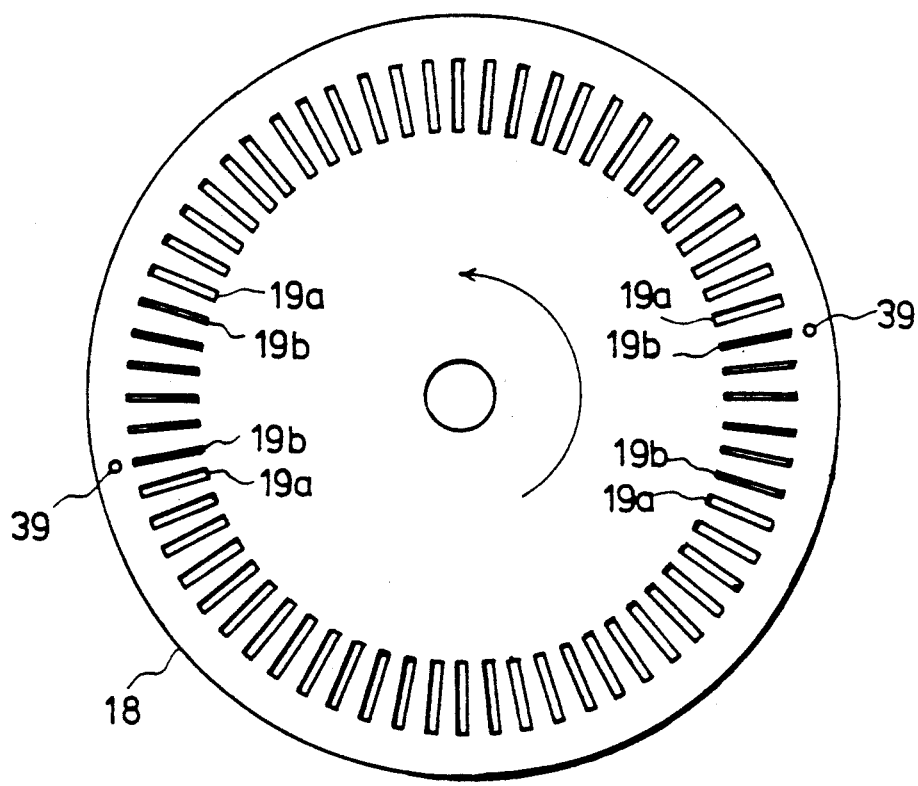
FIG. 4 is a plan view showing an embodiment of the light shielding rotary member used in the eyeball microscope according to this invention.

The light shielding discs 18 and 29 are of the same design and have a number of radial slits 19 (30) arranged at equal intervals, respectively, as shown in FIG. 4. As a feature of this invention, some of the slits 19 (30) (two groups having six slits each as shown) have a narrower width than the others. In the drawing, the wide slits are denoted by 19a (30a) and the narrow slits are denoted by 19b (30b). A pair of detection pinholes 39 are formed outside the leading ends of the groups of narrow slits 19b. The discs 18 and 29 are rotationally driven at high speed in synchronism with each other by a motor 37 through toothed pulleys 38 and a toothed belt 39.

Figure 5:
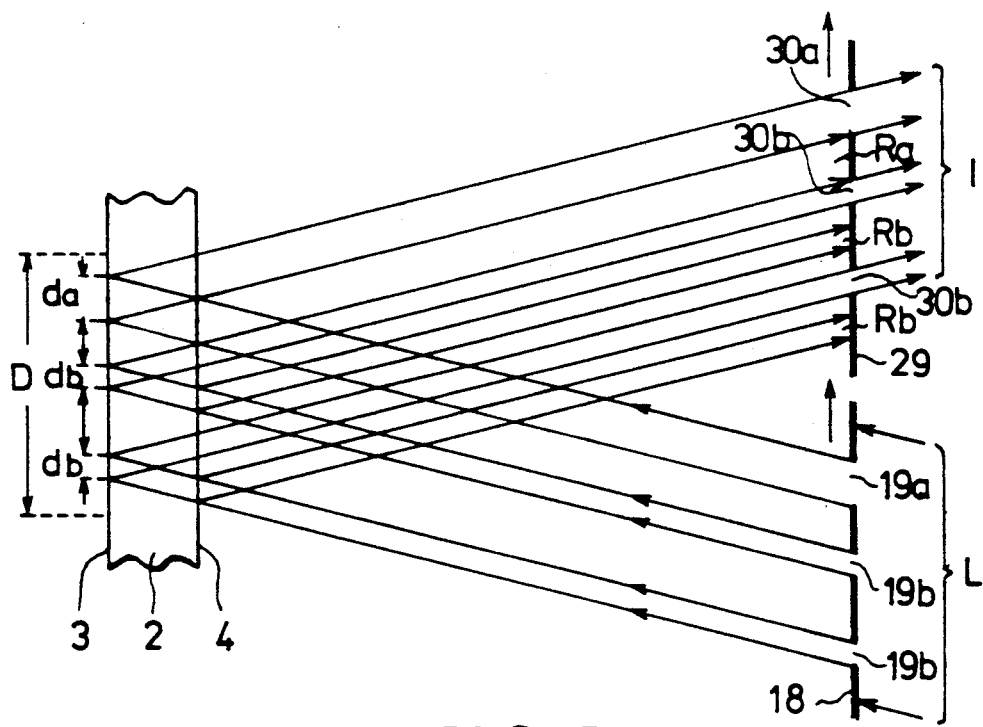
FIG. 5 is an explanatory diagram showing a mutual relationship of the illuminating, imaging and reflecting light beams in the eyeball microscope according to this invention.

As a result, in the case of observing the endothelial cell layer 3 of the cornea 2, as shown in FIG. 5, the illuminating beam L passing the slits 19a and 19b of the light shielding disc 18 illuminates the cornea 2 in a microscope field of view D in a pattern of stripes of widths $d_a$ and $d_b$ which are normal to the plane of paper. Although the imaging beam I is taken out through the slits 19a and 19b of the disc 29, the reflecting beams Ra and Rb produced at the cornea surface 4 miss the slits and are shut off by the disc 29. When the discs 18 and 29 are synchronously driven to move the slits 19 and 30 in the arrow direction, the endothelial cell layer 3 in the field of view D is scanned successively by a striped pattern of slit images to enable observation of the whole of it. In this case, the reflecting beam Ra does not obstruct so much eye observation, though it is apt to overlap the imaging beam I through the wide slit 30a of the disc 29 as shown. However, the reflecting beam Rb of the illuminating beam L from the narrow slit 19b of the disc 18 is completely shut off by the disc 29 and the imaging beam from the narrow slits 30b of the disc 29 does not include the reflecting beam Rb at all. When the leading end of the group of narrow slits 19b of the disc 18 traverses the optical path 40 of the illuminating optical system, a light beam from a light source 43 of FIG. 3 passes the detection pinhole 39 into a light sensor 44 and the sensor 44 drives the flashing discharge tube 23 through a control circuit as described below. Then, a photograph is taken on the film 35 since the control circuit is energized by a shutter of the camera 34. As described above, with the light shielding discs 19 and 29 of this invention, it is possible to obtain a bright image which facilitates focusing operation in eye observation since it is effected through the wide slits 19a and 30a and it is also possible to obtain a clear picture including no reflecting light in photographing since it is effected through the narrow slits 19b and 30b.

The thickness of cornea is about 0.5 mm in case of mankind, it is only about 0.2 mm to 0.3 mm in case of small animals for experiments. In order to accord with such variation in the cornea thickness, it is desirable to change the pitch or interval of the slits in the light shielding discs 18 and 29. In the embodiment of FIG. 3, this can be effected by combining the discs 18 and 29, the driving device 37, 38 and 39 and the detecting device 43 and 44 into a single unit and exchanging the same.

Figure 6:
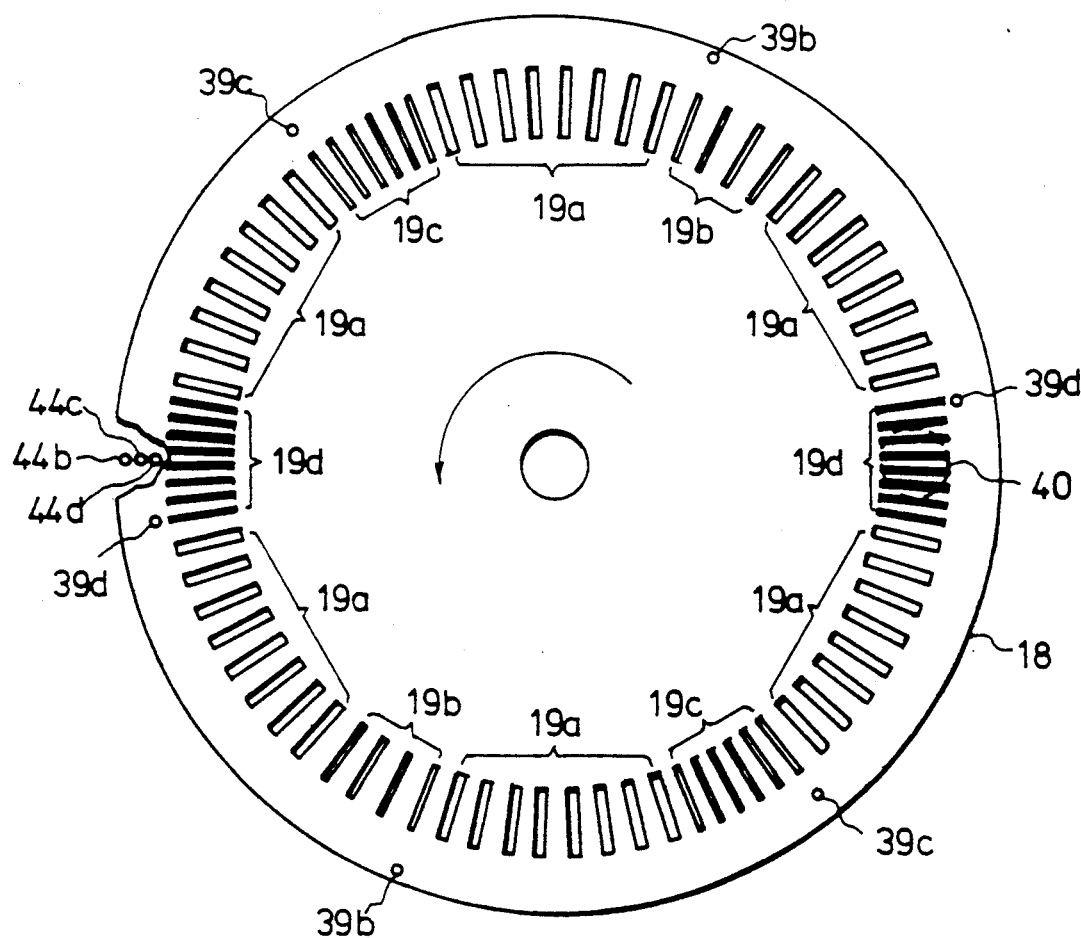
FIG. 6 is a plan view showing another embodiment of the light shielding rotary member used in the eyeball microscope according to this invention.

Accomodation to the variation of corneal thickness can be obtained also by changing the slit width instead of the slit pitch. The change of slit width can be attained by the disc 18 (and disc 29) as shown in FIG. 6, without exchanging the light shielding disc. As shown, this disc 18 has four kinds of slits 19a, 19b, 19c and 19d which are different in their widths and the widest slits 19a for eye observation are divided into six groups which are arranged at central angles of 60 degrees. The narrower slits 19b, 19c and 19d for photography are divided into two groups each and arranged symmetrically about the center between the respective groups of the slits 19a. This disc 18 also has pinholes 39b, 39c and 39d for detecting the photographing slits 19b, 19c and 19d at the leading ends of the respective groups of slits 19b, 19c and 19d. As shown, the pinholes 39b, 39c and 39d are radially displaced and sensors 44b, 44c and 44d for the respective groups are fixed on the same radius and on respective moving paths of the pinholes 39b, 39c and 39d so that they can face thereto.

Figure 7:
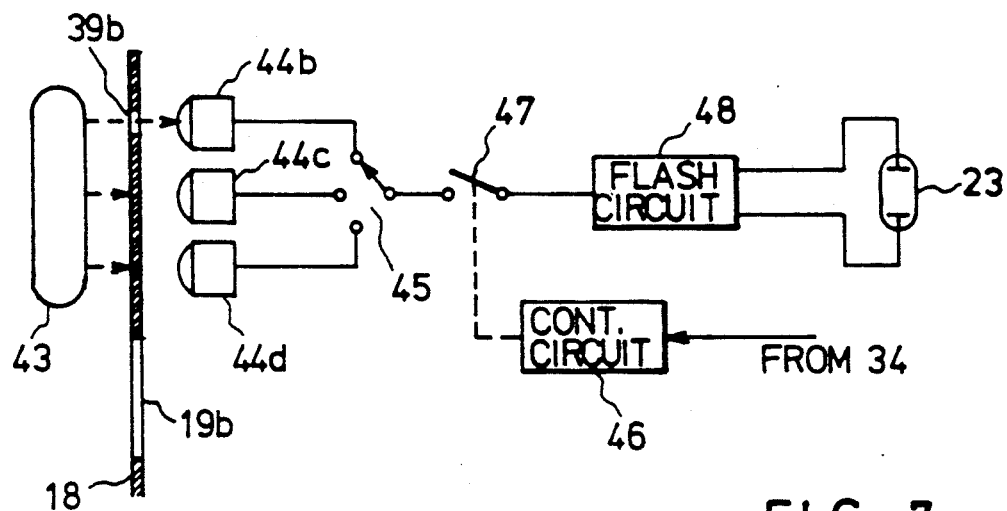
FIG. 7 is a schematic circuit diagram showing an example of flashing discharge tube driving device used with the light shielding rotary member of FIG. 6.

As shown in FIG. 7, the detection light source 43 is composed of a single light emitter and light sensors 44b, 44c and 44c facing respectively thereto through the disc 18 are connected through a change-over switch 45 and an ON/OFF switch 47 to a flashing circuit 48 for the flash discharge tube 23. The ON/OFF switch 47 is controlled by a driving circuit 46 which is connected to an X contact of the camera 34 so that it is closed when the shutter is opened. Accordingly, if the change-over switch 45 is manually operated to select the photographing slits of a desired width and the shutter of the camera 34 is pushed, the flash discharge tube 23 is flashed during traverse of the selected slits across the illuminating optical path 40 (shown in phantom circle). It is a matter of course that this flash control device can be used also with the light shielding discs of FIG. 4.

Figure 8:
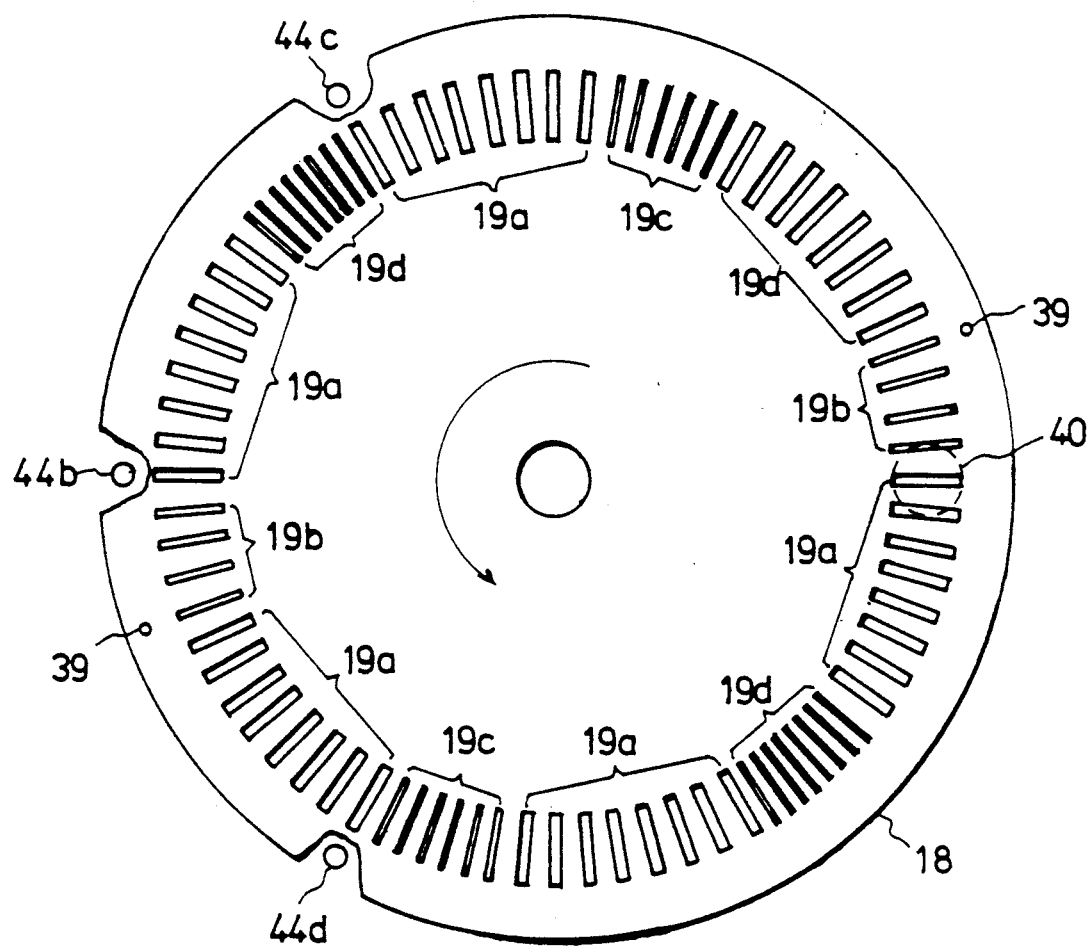
FIG. 8 is a plan view showing a modification of the light shielding rotary member of FIG. 6.

FIG. 8 shows a modification of the light shielding disc of FIG. 6. While this disc 18 has the same slit pattern as the disc of FIG. 6, only a pair of pinholes 39 are disposed on the same circle for detecting the photographing pinholes as in the disc of FIG. 4. As briefly shown in FIG. 8, however, three light sensors 44b, 44c and 44d and three corresponding light sources (now shown) are arranged at 60 degree intervals so that they can face the pinholes 39 and positioned with respect to the disc so that the respective groups of slits can be detected when they come in the illuminating optical path 40 (shown in phantom circle) of the microscope.

The above embodiments have been provided only for the purpose of illustration and do not mean any limitation of the range of invention. It should be noted that various modifications and changes can be applied to these embodiments without leaving the spirit and scope of this invention as defined in the appended claims. For example, if some structural difficulties are overcome, the above-mentioned two light shielding discs may be substituted with a single disc by using a pair of slit groups facing on the same diameter. While the object is scanned by a striped slit pattern in the above embodiments, it can be scanned by a single slit image if there is no problem of brightness. The detection pinhole 39 may be substituted with a suitable mark which is sensed by a light sensor of reflection type. If the mark is of a type including an identifying information, such as a bar code, plural groups of slits can be detected by a single detector. The photoelectric detector may be substituted with an electromagnetic or mechanical detector. The light shielding rotary member need not be a circular disc and it can take any other shape such as cylinder. It is also possible to remove the slits for eye observation and include only the slits for photography.

We claim:

1. An eyeball microscope comprising:
   a first lens to be positioned close to an object,
   second and third lenses located in the rear of respective halves of said first lens as viewed from said object,
   rotary light shielding means having a number of substantially parallel slits divided into at least two groups of different design and arranged to traverse an optical axis of said second lens in a conjugate focal plane of said object attributable to said first and second lenses and to traverse an optical axis of said third lens in a conjugate focal plane of said object attributable to said first and third lenses,
   an illuminating optical system including a flash discharge tube for projecting an illuminating light beam onto said object through at least one of said slits of said rotary light shielding means to form an image of said slit on said object,
   an observing optical system for observing or photographing an imaging light beam from said object through at least another slit of said rotary light shielding means belonging to the same group,
   a driving device for rotating said rotary light shielding means to move the slit image on said object normally thereto, and
   means for detecting a selected one of said groups of slits to energize said flash discharge tube.

2. An eyeball microscope as set forth in claim 1, wherein said groups of slits are mutually different in one of width and interval thereof.

3. An eyeball microscope as set forth in claim 1, wherein said detecting means includes an identification mark fixed to said rotary light shielding means, and photoelectric means for detecting said mark.

4. An eyeball microscope as set forth in claim 1, wherein said rotary light shielding means has the shape of a circular disc and said slits are arranged radially along the periphery thereof.

5. An eyeball microscope as set forth in claim 1, wherein said rotary light shielding means and said driving device are combined in a single unit which is detachable from a main body of said microscope.

6. An eyeball microscope as set forth in claim 1, wherein said rotary light shielding means includes a first light shielding rotary member having a number of substantially parallel slits divided into at least two groups of different design and arranged to traverse the optical axis of said second lens in the conjugate focal plane of said object attributable to said first and second lenses, and a second light shielding rotary member of the same design as said first light shielding rotary member, the slits of said second member being arranged to traverse the optical axis of said third lens in the conjugate focal plane of said object attributable to said first and third lenses, said driving means including means for synchronously rotating said first and second light shielding rotary members, whereby the groups of slits of the same design in said first and second rotary members traverse at the same time the optical paths of said illuminating and observing optical systems.

* * * * *